United States Patent [19]

Pearce et al.

[11] Patent Number: 5,403,267
[45] Date of Patent: Apr. 4, 1995

[54] ORTHOPEDIC BANDAGES WITH LOW MODULUS FILAMENTS

[75] Inventors: Richard H. Pearce; Roderick J. Hulme, both of North Humberside, United Kingdom

[73] Assignee: Smith & Nephew plc, United Kingdom

[21] Appl. No.: 47,248

[22] Filed: Apr. 14, 1993

Related U.S. Application Data

[63] Continuation of Ser. No. 657,838, Feb. 19, 1991, abandoned, which is a continuation of Ser. No. 299,264, Jan. 23, 1989, abandoned.

[30] Foreign Application Priority Data

Jan. 23, 1988 [GB] United Kingdom ............... 8801636

[51] Int. Cl.$^6$ .............. A61F 13/00; A61F 15/00; A61L 15/00
[52] U.S. Cl. ............................. 602/8; 602/1; 602/76; 66/192
[58] Field of Search .............. 66/192, 193; 427/2; 602/1, 5, 6, 8, 76

[56] References Cited

U.S. PATENT DOCUMENTS

| | | |
|---|---|---|
| 3,332,416 | 7/1967 | Brickman et al. |
| 3,881,473 | 5/1975 | Corvi et al. ............... 128/90 |
| 4,411,262 | 10/1983 | von Bonin et al. ............ 128/90 |
| 4,668,563 | 5/1987 | Buese et al. ............ 428/230 |
| 4,745,912 | 5/1988 | McMurray ............ 602/8 |

FOREIGN PATENT DOCUMENTS 301214  2/1989  European Pat. Off.

Primary Examiner—Paul Prebilic
Attorney, Agent, or Firm—Rosenman & Colin

[57] ABSTRACT

The present invention is directed to a water-hardenable orthopedic splinting bandage. The substrate comprises inelastic fibers being incorporated in the substrate in the lengthwise direction. In a preferred substrate, the low modulus fiber is a multifilament polypropylene and the elastic fiber is a polyurethane yarn. Comfomable orthopedic bandages employing the substrate are also described.

16 Claims, 1 Drawing Sheet

ORTHOPEDIC BANDAGES WITH LOW MODULUS FILAMENTS

This application is a continuation of U.S. patent application Ser. No. 07/657,838, now abandoned, which is a continuation of U.S. patent application Ser. No. 07/299,264, now abandoned.

The present invention relates to water hardenable orthopedic splinting bandages comprising a fabric substrate impregnated with a water-curable resin, for example, a resin containing isocyanate groups. More particularly, the present invention relates to an orthopedic bandage comprising a resin-coated fabric substrate which is stretchable in the lengthwise direction and to the substrate itself.

Conventionally, orthopedic splinting bandages for use in the treatment of bone fractures or other conditions requiring immobilization of part of the body are formed from a substrate impregnated with a substance which hardens to a rigid structure after wrapping the bandage around the body. Traditionally Plaster of Paris was used, but more recently, certain plastics have gained acceptance as replacements for Plaster of Paris. Such new bandages are lighter, waterproof and permeable to X-rays. One way in which strength is added to such casts is to use a glass fiber substrate which it is believed not only acts as a carrier for the resin but also reinforces the final cured bandage. This substrate is preferably a glass fiber fabric such as that described in U.S. Pat. Nos. 4,502,479, 4,609,578, 4,668,563 or 4,323,061.

One disadvantage of glass fiber casts is that they can become brittle and break down during wear and hence need to be replaced. A second disadvantage is that during cast removal irritating glass dust or fibers may be generated. These disadvantages would be mitigated by using a substrate which gave a durable cast and did not give rise to irritating fibers on cast removal. However, heretofore such substrates have lacked the conformability and cast strength found when using glass fiber substrates.

Surprisingly, it has been found that by using as a substrate a knitted fabric which comprises low modulus, inelastic fibers and elastic fibers incorporated in the lengthwise direction, a bandage is achieved which has good conformability compared to those employing existing glass fabric substrates. Even more surprisingly, the cast formed using this novel substrate has sufficient rigidity and can show no loss of strength compared to a cast which employs a glass fiber substrate. In addition it yields casts which are less brittle and can be more durable than some glass fiber based casts.

In one aspect, therefore, the present invention provides a knitted substrate suitable for use in a resin-coated, water hardenable orthopedic splinting bandage which substrate comprises inelastic fibers of low modulus of elasticity and elastic fibers, said elastic fibers being incorporated in the substrate in the lengthwise direction. Most suitably, the resin is a water curable resin so that the bandage is one which hardens after being exposed to water.

As is apparent herein, the term "fiber" relates to the material which is knitted whether that yarn is comprised of monofilaments or multifilaments.

Such knitting is illustrated by the drawing in which:

Figure 1:
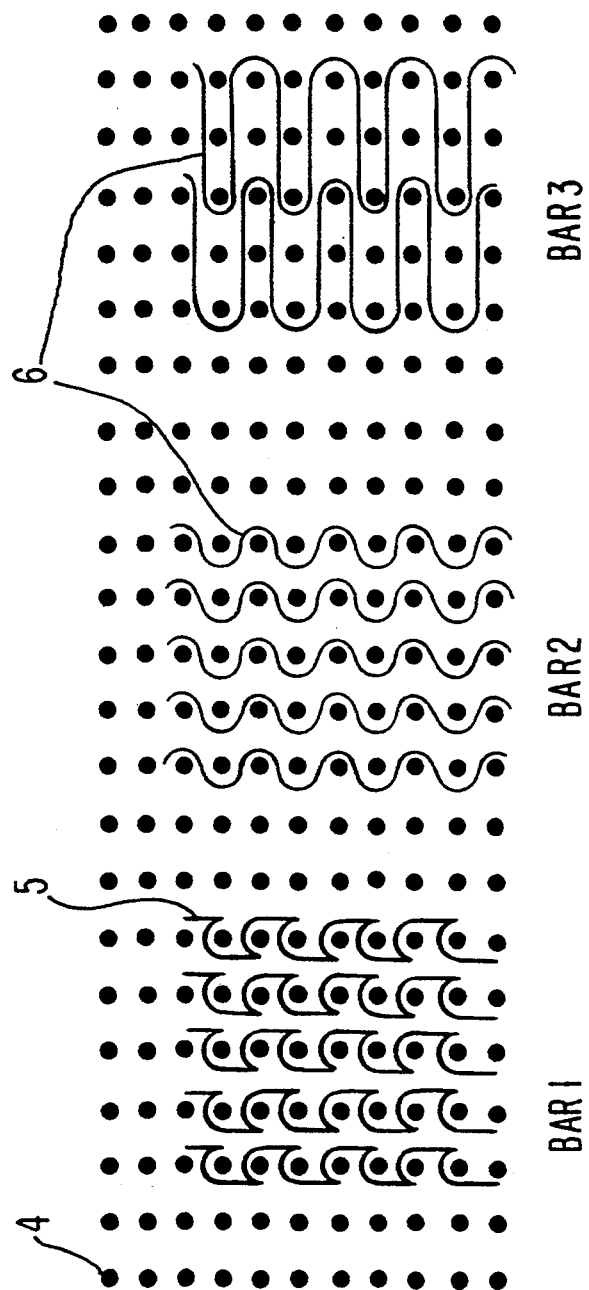
FIG. 1 illustrates a three bar Raschel knit, comprising needles (4), a chain stitch (5) and yarns (6). In operation, guide bar 1 performs a chain stitch (5) while guide bars 2 and 3 lay in a yarn (6).

The orthopedic splinting bandages of the present invention possess lengthwise extendability by virtue of the presence in the substrate of elastic fibers incorporated in the lengthwise direction of the bandage. Suitable elastic fibers may be formed from rubber or elastomeric polymers which have high extendability together with substantially complete and rapid elastic recovery. Suitable fibers may have an elongation at break in excess of 100% and more suitably in excess of 300%, for example 500 to 800%. Suitable elastic yarn (fibers) include those formed from natural rubber or a synthetic elastomer such as polyisoprene, polybutadiene, copolymers of a diene and styrene or acrylonitrile, polychloroprene or copolymers thereof, elastomeric ethylenepropylene copolymers and thermoplastic elastomers including block copolymers of styrene and butadiene or isoprene or an elastic polyurethane yarn. A preferred elastic fiber is a natural rubber fiber. A particularly preferred elastic fiber is a spandex fiber, that is a polyurethane fiber, for example, Lycra fiber (Trade mark). The successful use of such yarns as polyurethane yarns is surprising since the anticipated plasticization by polyurethane prepolymer resins does not occur to an extent which results in unacceptable weakening of the product.

The elastic fiber is present in the knitted substrate in the warp, that is, the machine direction. Suitably, about 0.5 to 20% of the volume of the substrate may be made up from elastic fibers and more suitably 1 to 8% of the volume of the substrate is made up from elastic fibers.

Suitably, the lengthwise extension of the substrate may be such as to give the resin coated substrate an extension of from 15% to 80% and more suitably, may be from 20% to 30%, for example, 25% when measured at a load of 640 gm per inch (2.5 cm).

Suitably, the widthwise extension of the substrate may be from 20 to 100%, more suitably 25 to 60% and preferably 30 to 50% for example 45% (when similarly measured).

Suitably, the substrate may be heat treated using steam to improve the stretch of the substrate and to provide a more consistent bandage after coating.

The elastic fibers in the substrate appear to cause the substrate to return to its original length after stretching and so facilitates conformability of the substrate to the patient's body. The bandages were observed to conform easily to various shaped formers made to represent parts of the body.

Suitably, the knitted substrate has a low power, that is the force required to stretch the substrate for a given percentage extension. If this power is low then this will help to prevent constriction of the patient's limb after the bandage has been applied. Suitably the power can be less than 20 g cm$^{-1}$ width at 10% extension, more suitably less than 15 g cm$^{-1}$ width and preferably less than 10 g cm$^{-1}$ width at 10% extension.

The lengthwise extension may be measured using an Instron Tensile Testing Machine. A 10 cm length of substrate may be clamped in the jaws of the machine and the jaws separated at constant speed. A conventional stress-strain curve for the substrate may be recorded. The extension at a given load and the load required to give a given extension can be calculated from the curve for the substrate under test.

The remainder of the knitted substrate may be formed from a fiber (yarn) which is a low modulus fiber, that is, a fiber which has a modulus of elasticity of less than $10^5$ psi and suitably, less than $2 \times 10^4$ psi and more suitably, less than $10^4$ psi. Individual filaments within the fiber include those which have a modulus of less than $3 \times 10^6$, more suitably, less than $2 \times 10^6$ and preferably, less than $10^6$ and include polymer fibers such as polypropylene, polyester, polyamide and polyethylene. A preferred fiber is formed from polypropylene and may be employed as a multifilament or monofilament fiber. A second preferred fiber is polyester including multifilament or monofilament polyethylene terephthalate fiber. The use of such yarns leads to particularly durable casts.

Suitably, the substrate may have a thickness of from 0.375 mm to 1.25 mm, more suitably will be 0.45 mm to 1.0 mm thick and preferably, 0.50 mm to 0.875 mm thick, for example, 0.825 mm.

Suitably the knitted substrate may have a weight per unit area of from 50 to 500 $gm^{-2}$, more suitably, may have a weight of from 100 to 350 $gm^{-2}$ and preferably, a weight of between 170 and 270 $gm^{-2}$, , for example, 250 $gm^{-2}$.

Suitably the substrate will be in the form of a flexible fabric which has been knitted. Suitable knit-types for the substrate are described in, for example, U.S. Pat. Nos. 4,427,002, 4,502,479, 4,609,578 and 4,668,563. Suitable fabrics may be employed as a Raschel knit, a crochet knit or a tricot knit. A preferred substrate will be in the form of a warp knitted fabric having a chain stitch along its length. A knitted fabric may be formed on a 3-bar knitting machine in which the first bar usually carries a low modulus fiber and is arranged to knit open lap stitches or closed lap stitches. The second bar usually carries the elastic fiber which can be knitted in with the fiber on the first bar or can be laid in. The third bar usually carries a low modulus fiber which is laid in a zig-zag pattern across the fabric. The number of wales crossed by the fiber on the third bar can be used to control the width wise stretch, substrate weight and substrate dimensional stability.

One suitable knit pattern is described in U.S. Pat. No. 4,427,002 at column 3, line 33 to column 5, line 4. Unfortunately this earlier fabric was only poorly conformable. The knit is aptly of a type which can mitigate against formation of frayed ends when the substrate is cut. The use here of fibers other than glass fiber also helps prevent the generation of stiff fiber ends which stick out from the set cast which may irritate the wearer and cast technician and give rise to a rough appearance to the cast. The use of low modulus fibers which bend easily allows smooth casts to be achieved especially at the edges. This is a considerable advantage as special treatments of fibers or the knitted substrate can be avoided.

. Suitably, the substrate may be a mesh, that is, it should have openings through it to enable the curing agent to penetrate into the rolled bandage to contact all parts of the resin. The openness of the substrate will also permit circulation of air to and evaporation of moisture from the skin beneath the cured bandage. The mesh may be defined by counting the number of repeating patterns of the knit on a square inch of the fabric. This may be accomplished by taking a photograph of a section of the substrate when relaxed at known magnification and counting the recurring units across and along the section for a distance equivalent to an inch in each direction and multiplying the two figures together. Suitably the fabric may have a mesh of from about 200 to 300 per sq. inch, more suitably, from 220 to 270 per sq. inch and preferably 240 to 260 per sq. inch, for example 240, 250 or 260 per sq. inch.

In one favored embodiment the present invention provides a knitted substrate suitable for use in a resin-coated, water-hardenable orthopedic splinting bandage which substrate comprises inelastic fibers of low modulus of elasticity and elastic fibers, said elastic fibers being incorporated in the substrate in the lengthwise direction in an amount of from 1 to 8% by volume of the substrate, said substrate having a lengthwise extension of from 15 to 80%.

In a second favored embodiment the present invention provides a knitted substrate suitable for use in a resin-coated, water-hardenable orthopedic splinting bandage which substrate comprises an inelastic fiber of modulus less than $2 \times 10^4$ psi and elastic fibers, said elastic fibers being incorporated in the substrate in the length direction in an amount of from 1 to 8% by volume of the substrate, said substrate when resin coated having a lengthwise extension of from 20 to 30%.

In a preferred embodiment the present invention provides a knitted substrate suitable for use in a resin-coated, water-hardenable orthopedic splinting bandage which substrate comprises inelastic polypropylene fibers of modulus less than $2 \times 10^4$ psi and elastic polyurethane fibers, said elastic fibers being incorporated in the lengthwise direction in an amount of from 1 to 8% by volume of the substrate, said substrate when resin coated having a lengthwise extension of from 20 to 30%.

The resins used in the orthopedic bandage of the invention may be any curable resin which will satisfy the functional requirements of an orthopedic cast. The preferred resins are those cured with water or moisture and include the resins described in U.S. Pat. Nos. 4,667,661, 4,502,479, 4,574,793, 4,433,680, 4,427,002, 4,411,262, 3,932,526, 3,908,644, 3,630,194, in German Offenlegungsschrift No. 2651089 and in European Patent Applications Nos. 35517, 57988, 86621 and 94222.

Aptly, the resin used to coat the fiber substrate may be a water curable isocyanate terminated prepolymer system. Among suitable prepolymer systems are those identified in U.S. Pat. Nos. 4,411,262, 4,427,002, 4,433,680 and 4,574,793. Particularly preferred are those systems disclosed and claimed in U.S. Pat. Nos. 4,427,002 and 4,574,793 the disclosures of which are incorporated herein by cross-reference.

Suitably, the bandage may be formed by coating or impregnating the substrate with the resin in the manner described in those patents, particularly in U.S. Pat. No. 4427002.

Suitably, the weight of resin on the substrate may be from 150 to 500 $gm^{-2}$, more suitably, a weight of 200 to 450 $gm^{-2}$ and preferably, between 250 to 400 $gm^{-2}$. The weight of resin may be chosen so that suitably 40 to 60% of the total weight of bandage is resin and more suitably 50 to 55% of the total weight. Thus if the fabric weight is 25O $gm^{-2}$ and the resin coating is 55-60% of the bandage then the weight of resin taken is 305-375 g.

For the best shelf life of resin coated substrates, the elastic fiber used in the substrate must be compatible with the resin with which it is coated. Suitable compatible elastic fibers may be identified by forming a bandage incorporating the elastic fiber and coating with the desired resin and ageing in a sealed container for 12 weeks at 55° C. If at the end of this time the bandage may be used to form a satisfactory cast, then the elastic fiber is particularly suitable for use in conjunction with the resin. Difficulties with elastic fibers may be overcome by means of coating or wrapping the fiber with inert materials such as cotton or nylon yarn.

The formed bandages may be packaged by heat sealing in waterproof pouches such as those formed from metal foil polyethylene laminates or polyethylene pouches.

In use the bandages may be brought into contact with water and wrapped around the injured part of the body. The setting bandage has a working time which is sufficient to allow the bandage to be positioned on the limb and a set time which is the time taken for the cast to become rigid. Apt working times are 1 to 6 minutes and apt set times are 5 to 30 minutes.

The cast incorporating the substrate of the invention is readily removable by conventional means such as by cutting with a conventional circular saw. Large casts may be removed using a single cut along the length of the cast which is not always achievable with fiber glass substrate casts. The use of polypropylene or polyester in the substrate makes cast removal easier and does not generate glass dust or fibers.

The build-up of strength in the cast was assessed by wrapping the resin-coated substrate round a former to make a cylinder. The former is removed and the cylinder wall clamped in an Instron Tensile Testing Machine so as to measure diametral compression and extension forces. The machine is adapted so that the moving clamp would oscillate between positions 2.5 mm from the rest position. The force required to deform the cast as it set over a period of time is measured. The results were recorded on a chart recorder. A bandage formed according to Example 2 was tested in comparison with a conventional glass fiber based bandage using cylinders formed of 5 layers of bandage. The bandage according to the invention was comparable in strength to the glass fiber bandage both on initial setting and after 24 hours.

|  | Rigidity (kg/cm width) Time after initiation of set | | |
| --- | --- | --- | --- |
|  | 15 mins | 30 mins | 24 hr |
| Bandage of Example 2 | 2.0 | 2.7 | 4.7 |
| Glass fiber-based bandage | 2.1 | 2.65 | 4.5 |

The durability of a cast formed from a bandage of the invention areas tested by applying leg casts to volunteers which they wore for 48 hours during which they walked between 6 and 40 km. No break down in the casts was observed. In a comparative trial using a conventional glass fiber cast 30% of the casts were observed to have broken down at the end of the trial period.

In one favored embodiment, the present invention provides a conformable water-hardenable orthopedic splinting bandage comprising a knitted substrate coated with a water curable resin which substrate comprises inelastic fibers of low modulus of elasticity and elastic fibers, said elastic fibers being incorporated in the substrate in the lengthwise direction in an amount which comprises from 1 to 8% by volume of the substrate and which resin coated substrate has an extension in the lengthwise direction of 15 to 80%.

In a particular preferred embodiment, the present invention provides a conformable water-hardenable orthopedic splinting bandage comprising a knitted substrate coated with a water curable resin which substrate comprises inelastic polypropylene fibers of modulus less than $2 \times 10^4$ psi and elastic polyurethane fibers, said elastic fibers being incorporated in the lengthwise direction in an amount which comprises from 1 to 8% by volume of the substrate, said resin coated substrate having a lengthwise extension of from 20 to 30%.

EXAMPLE 1

Preparation of Substrate

A substrate is prepared by knitting together elastic polyurethane fibers and a low modulus fiber of polypropylene. The elastic polyurethane fibers are formed from a segmented polyurethane and are commercially available as Lycra spandex fibers. The polyurethane fiber is wrapped in nylon or cotton yarn. The polypropylene is a 70 filament yarn of weight per unit length of 470 d Tex. The knit-type is a Raschel 3-bar warp knit in which the first bar is full set at 0-1/1-0 and carries polypropylene fiber, the middle bar is full set at 0—0/1—1 and carries polyurethane fiber and the third bar is full set at 0—0/3—3 and carries polypropylene fiber. The substrate is knitted as a long strip with a width of 10 cm, when relaxed there are approximately 6.0 to 7.9 courses/cm and 4 to 6 wales/cm and a weight per unit area of 200 $gm^{-2}$.

The knitted fabric when coated with resin has an extension in the widthwise direction of 80% and extension in the lengthwise direction of 25%.

EXAMPLE 2

Preparation of Bandages

A water curable polyurethane resin system comprising a polyurethane prepolymer described in U.S. Pat. No. 4,574,793 as prepolymer A and containing methane sulphonic acid as stabilizer and bis(2,6 dimethylmorpholino)diethyl ether as catalyst is coated onto a knitted substrate described in Example 1 using the process described in U.S. Pat. No. 4,427,002. The weight of the resin applied is 240 $gm^{-2}$ which means that the resin forms 55% of the weight of the bandage.

The bandage strip is cut into 3 meter lengths and spooled onto rolls. The bandage rolls are then placed in pouches which are heat sealed to prevent exposure of the contents to moisture.

A bandage is made into a cast by dipping the bandage roll in water and wrapping around a body member.

EXAMPLE 3

Preparation of Bandages

A viscous prepolymer comprising a purified polyethylene glycol isocyanate terminated prepolymer prepared in the same manner as that described in Example 22 of European Patent Application No. 57988.

A slurry is prepared by mixing a solution of the prepolymer in dry methylene chloride with potassium carbonate, alumina, Sylosiv A3 and Desmodur M44.

A slurry is coated by means of a doctor blade onto a 10 cm wide strip of a warp knit substrate comprising an elastic polyurethane fiber and a low modulus polypropylene fiber. The substrate may be stretched by up to 25% when subjected to tension. The coating is formed at a weight per unit area of 250 g/m². The bandage strip is cut into 1 meter lengths and spooled onto rolls. The bandage rolls are then heat sealed into pouches of low density polyethylene.

EXAMPLE 4

Preparation of Substrate

A substrate is prepared by knitting together elastic polyurethane fibers and a polyester fiber. The elastic polyurethane fibers are formed from a segmented polyurethane and are commercially available as Lycra spandex fibers. The polyurethane fiber is wrapped in nylon or cotton yarn. The polyester is a 1000 denier multifilament polyethyleneterephthalate. The knit-type is a Raschel knit using approximately 2 to 3 wales/cm width and 5 to 6 courses/cm length.

The knitted fabric has an extension in widthwise direction of 60% and extension in the lengthwise direction of 25%.

The substrate may be coated with a moisture curable resin as described in Example 2 to form a bandage which is thereafter packaged in a waterproof pouch and used by removing the bandage from the pouch, dipping in water and wrapping around a body member.

EXAMPLE 5

Preparation of Substrate

A substrate is prepared by knitting together elastic polyurethane fibers and a low modulus fiber of polypropylene. The elastic polyurethane fibers are formed from a segmented polyurethane. The polyurethane is wrapped, is shown in FIG. 1 in nylon or cotton yarn. The polypropylene fiber is a 70 filament yarn with a weight per unit length of 470 dTex. The warp knitted fabric is of a Raschel 3-bar knit-type in which the first bar is full set at 0-1/1-0 and carries polypropylene fiber, the middle bar is full set at 0—0/1—1 and carries polyurethane fiber and the third bar is half set at 0—0/3—3 and carries polypropylene fiber. The substrate is knitted as a long strip at a width of 10 cm. With the fabric in a relaxed state there are approximately 6.0 to 7.9 courses/cm and 4 to 6 wales/cm. The fabric has a weight per unit area of 160 gm$^{-2}$. The fabric therefore has a more open appearance that the substrates of Examples 1 and 4 and thereby slightly improved moisture vapor permeability properties.

The knitted fabric when coated with resin has an extension in the widthwise direction of 60% and extension in the lengthwise direction of 25%.

The substrate may be coated with a moisture curable resin as described in Example 2 to form a bandage which is thereafter packaged in a waterproof pouch and used by removing the bandage from the pouch, dipping in water and wrapping round a body member. If the weight of resin applied is 240 gm$^{-2}$ then this forms 60% of the weight of the bandage.

EXAMPLE 6

Preparation of Substrate

A substrate was prepared by knitting together an elastic Lycra fiber comprising a polyurethane yarn wrapped in crimped nylon yarn, in which the fiber has a weight per unit length of 78 dTex and a polypropylene fiber comprising a 70 filament yarn with a weight per unit length of 470 dTex. The substrate was knitted on a 3-bar machine in which bar 1 is full set at 0-1/1-0 and carries polypropylene fiber, bar 2 is full set at 0—0/1—1 and carries the Lycra fiber and bar 3 is full set at 0—0/3—3 and carries polypropylene fiber which is laid in across 3 wales. The fabric has 6.4 to 7.2 courses per cm and 5.4 to 5.7 wales per cm. This results in a fabric having a weight of approximately 220 gm$^{-2}$ and 244 openings per sq in. The fabric has a lengthwise stretch at 640 gm$^{-1}$ width of 48% and 25% when coated with resin.

A sample of the substrate prepared above was coated with the resin described in Example 2. The resin coating was applied at a weight of 248 gm$^{-2}$ (approximately) which means that the resin forms 53% by weight of the bandage.

A bandage strip was prepared by cutting the coated substrate into strips 10 cm wide and 3 meters long. The strip may be spooled onto rolls and placed in moisture pouches which are heat sealed.

A bandage strip was removed from a pouch, dipped in water and wrapped around a body member. The bandage had a working time of 3-½ minutes and formed a rigid durable cast.

EXAMPLE 7

Preparation of Substrate

A substrate was prepared in a similar way to that described in Example 6 except that the elastic yarn was laid into the wale and that bar 3 was not half set. The fabric has 6.4 to 7.2 courses per cm and from 5.8 to 6.1 wales per cm. The resulting fabric had a weight per unit area of 240 gm$^{-2}$ and 261 openings per sq in. The fabric has lengthwise stretch at 640 gcm$^{-1}$ of 60% and of 30% when coated with resin.

A sample of the substrate was coated with the resin described in Example 2. The resin coating was applied at a weight per unit area of 283 gcm$^{-2}$ which means that the resin forms 54% by weight of the bandage.

The bandage formed from the coated substrate when dipped in water and wrapped around a body member formed a rigid, durable cast. The bandage was observed to have a working time of 3-½-4 minutes.

We claim:

1. A knitted substrate suitable for use in a resin-coated, water-hardenable orthopedic splinting bandage, said substrate comprises a warp knitted fabric having a chain stitch in the warp direction thereof and comprises inelastic fibers of low modulus of elasticity selected from the group consisting of polypropylene and polyester fibers, and elastic fibers, said elastic fibers being knitted in with or laid into said chain stitch and said inelastic fibers comprising filaments having a modulus of less than $3 \times 10^6$ psi.

2. A substrate according to claim 1 in which the substrate has an extension in the warp direction of from 15% to 80% and an extension in the weft direction of from 20% to 100%.

3. A substrate according to claim 1 in which the substrate has a weight per unit area of from 50 to 500 gm$^{-2}$ and from 200 to 300 openings per square inch.

4. A substrate according to claim 1 in which the elastic fibers are natural rubber fibers or polyurethane fibers.

5. A knitted substrate suitable for use in a resin-coated, water-hardenable orthopedic splinting bandage, said substrate comprising a warp knitted fabric having a chain stitch in the warp direction thereof and comprises inelastic fibers of low modulus of elasticity selected from the group consisting of polypropylene and polyester fibers, and elastic fibers, said elastic fibers being knitted in with or laid into said chain stitch and said inelastic fibers comprising filaments having a modulus of elasticity of less than $3 \times 10^6$ psi, and in which the inelastic fibers have a modulus of elasticity of less than $2 \times 10^4$ psi.

6. A substrate according to claim 5 in which the inelastic fibers of low modulus of elasticity are polypropylene fibers.

7. A substrate according to claim 5 in which the inelastic fibers of low modulus of elasticity are polyethylene terephthalate fibers.

8. A conformable water hardenable orthopedic splinting bandage comprising a knitted substrate coated with a curable resin wherein said substrate is a warp knitted fabric having a chain stitch in the warp direction thereof and comprises inelastic fibers of low modulus of elasticity selected from the group consisting of polypropylene and polyester fibers, and elastic fibers, said elastic fibers being incorporated in said chain stitch, and wherein said inelastic fibers comprise filaments having a modulus of elasticity of less than $3 \times 10^6$ psi.

9. A bandage according to claim 8 in which the resin is a water curable isocyanate terminated prepolymer system.

10. A bandage according to claim 8 in which the substrate when coated with resin has an extension in the warp direction of from 15% to 80% and an extension in the weft direction of from 20% to 100%.

11. A bandage according to claim 8 in which the uncoated substrate has a weight per unit area of from 50 to 500 $gm^{1\,2}$ and the weight of the resin is 40 to 50% of the total weight of the bandage.

12. A bandage according to claim 8 in which the elastic fibers are natural rubber fibers or polyurethane fibers.

13. A conformable water hardenable orthopedic splinting bandage comprising a knitted substrate coated with a curable resin wherein said substrate is a warp knitted fabric having a chain stitch in the warp direction thereof and comprises inelastic fibers of low modulus of elasticity selected from the group consisting of polypropylene and polyester fibers, and elastic fibers, said elastic fibers being incorporated in said chain stitch, and wherein the inelastic fibers have a modulus of elasticity of less than $2 \times 10^4$ psi.

14. A bandage according to claim 13 in which the inelastic fibers of low modulus of elasticity are polypropylene fibers.

15. A bandage according to claim 13 in which the inelastic fibers of low modulus of elasticity are polyethylene terephthalate fibers.

16. A bandage according to claim 8 in which the weight of the resin on the substrate is from 150 to 500 $gm^{-2}$.

* * * * *